United States Patent [19]
Kruse et al.

[11] Patent Number: 5,859,027
[45] Date of Patent: Jan. 12, 1999

[54] ANTIMICROBIAL AGENT

[75] Inventors: Lawrence Ivan Kruse, Claremont, N.H.; Sheldon E. Broedel, Jr., Catonsville, Md.

[73] Assignee: ChekTec Corporation, Baltimore, Md.

[21] Appl. No.: 805,176

[22] Filed: Feb. 26, 1997

Related U.S. Application Data

[60] Provisional application No. 60/056,921 Feb. 26, 1996.
[51] Int. Cl.[6] ........................ A61K 31/445; A61K 31/38; A61K 31/385; A61K 31/335
[52] U.S. Cl. ........................ 514/315; 514/430; 514/432; 514/434; 514/449; 514/451; 514/456
[58] Field of Search ..................... 514/315, 430, 514/432, 434, 449, 451, 456

[56] References Cited

U.S. PATENT DOCUMENTS

| | | | |
|---|---|---|---|
| 2,053,095 | 9/1936 | Maximoff | 260/96 |
| 2,417,584 | 3/1947 | Birkinshaw et al. | 195/36 |
| 4,196,280 | 4/1980 | Umezawa et al. | 536/17 R |
| 4,255,564 | 3/1981 | Umezawa et al. | 536/17 R |
| 5,189,150 | 2/1993 | Zeeck et al. | 536/6.5 |
| 5,217,990 | 6/1993 | Hansske et al. | 514/450 |

FOREIGN PATENT DOCUMENTS

WO 95/19706  7/1995  WIPO .

OTHER PUBLICATIONS

Chemical Abstract (122:234931) Sakuda et al., 1995.
Closse et al., "Isolierung und Konstitutionsermittlung von Chrysodin", *Helvetica Chemica Acta*, 56:Fasc. 1, Nr. 276, pp. 2694–2698, 1973.
Steyn et al., "The Structure of Dihydrodeoxy–8–epil–austdiol and the Absolute Configuration of the Azaphilones", *J.C.S. Perkin I*, pp. 204–206, 1976.
Anke et al., "Deflectins, New Antimicrobial Azaphilones From Aspergillus Deflectus", *The Journal of Antibiotics*, 35:No. 8, pp. 923–928, 1981.
Haraguchi et al., "Chrysodin, An Antifungal Antimetabolite", *Agric Biol. Chem.*, 54(8):2167–2168, 1990.
Chen, et al., "The Chemistry of Fungi, Part LXIV, The Structure of Monascin: The Relative Sterochemistry of the Azaphilones", *J. Chem. Soc.* (C), pp. 3577–3579, 1991.
Yasukawa et al., "Azaphilones Inhibit Tumor Promotion By 12–O–Tetra–Decanoylphorbol–13–Acetate In Two–Stage Carcinogenesis In Mice", *Oncology*, 51:108–112, 1994.
Sakuda et al., "Structure of Patulodin, A New Azaphilone Epoxide, Produced by *Penicillium urticae*", *The Journal Of Antibiotics*, 48:No. 1, pp. 85–86, 1995.

*Primary Examiner*—Kevin E. Weddington
*Attorney, Agent, or Firm*—Dechert Price & Rhoads

[57] ABSTRACT

The invention provides a method of treating a fungal infection comprising administering to an animal having a fungal infection a composition comprising an infection treating effective amount of a compound of formula I, wherein said compound is the following or a pharmaceutically acceptable salt of the following:

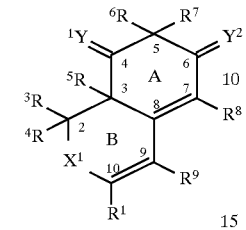

The invention further provides such compounds and related methods.

28 Claims, No Drawings

ANTIMICROBIAL AGENT

This application is a continuation of a provisional application 60/056,921 filed Feb. 26, 1996.

ANTIMICROBIAL AGENT

This application relates to novel antibiotics, which are particularly useful as antifungal agents, and to methods of treating microbial diseases.

The incidence of fungal infections has increased significantly over the last decade. This increase is in part due to the increase in the number of individuals who are immunologically compromised due to disease or to therapies that cause immuno-suppression. Since only a limited number of antifungal agents are available, the increased incidence of fungal infections has intensified efforts to identify new antimicrobial agents that are effective against fungal infections. The relative shortage of effective antifungal agents can to some extent be attributed to the similarity between eukaryotic fungal cells and the eukaryotic cells of the treatment subject, which similarly decreases the range of possible chemotherapeutic targets that can be used to selectively kill or inhibit the fungal cells while allowing the treatments subjects cells to continue to function.

Available antifungal agents include azoles such as fluconazole, itraconazole and the like and polyenes such as amphotericin B. These azoles and polyenes are believed to exploit differences in the content of fungal cell membranes versus the membranes of higher eukaryotes. In particular, fungal membranes differ in relying on ergosterol rather than cholesterol to increase the structural integrity of membranes. Azoles are believed to function by inhibiting ergosterol synthesis, while polyenes are believed to directly destabilize fungal membranes. For some fungal infections, the nucleoside analog 5-fluorouracil has been effective. The use of the azole, polyene and nucleoside analog agents described above is limited by their toxicity (see Vanden Bossche et al., *J. Med. Vet. Mycol.* 32(Suppl 1): 189, 1994; and Kennedy et al., *Transplantation* 35: 211, 1983) and the emergence of resistant fungi (see Odds, *J. Antimicrob. Chemother.* 31: 463, 1993; and McCullough and Hume, *J. Med. Vet. Mycol.* 33: 33, 1993).

Other therapeutic targets include the fungal cell wall, against which lipopeptides (for instance the echinocandin and papulacandin classes of agents) and peptide nucleosides (for instance the polyoxins and nikkomycins) have been targeted. These agents are limited by their narrow therapeutic spectrum. Further targets include the elongation factor EF3, which is believed to be unique to fungi, and fungal DNA topoisomerase.

Common metabolic enzymes have not been generally viewed as a likely therapeutic target given the likelihood of cross-inhibition of the disease host's metabolism. However, applicants have found certain compounds that may inhibit fatty acid synthetase ("FAS") have now been identified and shown to effectively treat fungal infections in mammals. This finding is surprising since both the infective fungal cells and the host of the fungal disease share the need to synthesize fatty acids using FAS enzymes.

SUMMARY OF THE INVENTION

The present invention provides compounds of formula I and a method of treating a fungal infection comprising administering to an animal, preferably a mammal, more preferably a human, having a fungal infection a composition comprising an infection treating effective amount of a compound of formula I. In the method, a compound of the following formula I is administered:

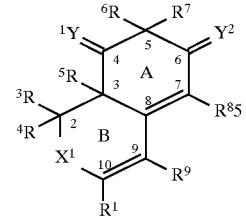

or a pharmaceutically acceptable salt thereof, wherein
(1) $Y^1$ and $Y^2$ are independently O or S;
(2) $R^1$
  (i) is a straight-chained aliphatic group having about 2 to about 12 carbon atoms,
  (ii) the aliphatic group which additionally comprises an about 3 to about 8-membered carbocyclic ring consisting of three or more additional carbon atoms, or
  (iii) the aliphatic group which additionally comprises an about 3 to about 8-membered heterocyclic ring, wherein the heterocyclic ring contains up to 4 nitrogen atoms, up to 2 sulfur atoms, up to 2 oxygen atoms or additional carbon atoms provided the resulting heterocycle is chemically stable,
    (2a) wherein the carbocyclic or heterocyclic ring atoms can have 1 to 4 substituents chosen from one or more of the following groups functional groups known in the art including but not limited to fluoro, chloro, bromo, iodo, hydroxy, (C1–C6) alkoxy, (C1–C6) alkyl, amino which can be substituted with one or two (C1–C3) alkyl groups, nitro, aminocarbonyl which can be N-substituted with one or two (C1–C6) alkyl groups, alkylcarbonyloxy wherein alkyl can be C1–C6, alkoxycarbonyl wherein alkoxy can be C1–C6, hydroxycarbonyl, cyano, (C1–C3) alkylsulfonamido, (C1–C3) haloalkylsulfonamido which can be fully or partially halogenated wherein halo is fluoro, chloro, bromo or iodo, (C1–C8) alkanoylamino, (C1–C3) haloalkyl, which can be fully or partially halogenated wherein halo is fluoro, chloro, bromo or iodo, alkanoylalkyl wherein alkanoyl is C2–C6 and alkyl is C1–C6and the like;
    (2b) wherein the non-ring portions of the straight-chained aliphatic group can be substituted with up to 4 of a (C1–C6) aliphatic group, fluoro, chloro, bromo, iodo, hydroxy, (C1–C6) alkoxy, amino which can be substituted with one or two (C1–C3) alkyl groups, nitro, aminocarbonyl which can be N-substituted with one or two (C1–C6) alkyl groups, alkylcarbonyloxy wherein alkyl can be C1–C6, alkoxycarbonyl wherein alkoxy can be C1–C6, hydroxycarbonyl, cyano, (C1–C3) alkylsulfonamido, (C1–C3) haloalkylsulfonamido which can be fully or partially halogenated wherein halo is fluoro, chloro, bromo or iodo, (C1–C8) alkanoylamino, (C1–C6) alkyl, (C1–C3) haloalkyl, which can be fully or partially halogenated wherein halo is fluoro, chloro, bromo or iodo, or alkanoylalkyl wherein alkanoyl is C2–C6 and alkyl is C1–C6 and the like;
(3) X is oxygen or sulfur or $NR^2$;
(4) $R^2$ is hydroxy, amino which can be substituted with one or two (C1–C8) alkyl groups, (C1–C8) alkyl, (C7–C10) arylalkyl, (C1–C8) alkoxy, (C1–C8) alkanoylamino or aminocarbonyl which can be N-substituted with one or two (C1–C8) alkyl groups and the like, wherein $R^2$ can be substituted with up to 4 of alkylcarbonyloxy wherein alkyl can be C1–C6, alkoxycarbonyl wherein alkoxy can be C1–C6, hydroxycarbonyl, fluoro, chloro, bromo, iodo, hydroxy, (C1–C3) alkoxy, amino which can be substituted with one or two (C1–C6) alkyl groups, nitro, aminocarbonyl which can be N-substituted with one or two (C1–C6) alkyl groups, cyano, (C1–C3) alkylsulfonamido, (C1–C8) alkanoylamino, (C1–C3) haloalkylsufonamido, (C1–C3) alkyl, (C1–C3) haloalkyl, or alkanoylalkyl wherein alkanoyl is C2–C3 and alkyl is C1–C3 and the like;

(5) $R^3$ and $R^5$ either (a) represent a common oxygen forming an epoxide, (b) each represent a half bond that together forms a double bond, or (c) $R^3$ is hydrogen and $R^5$ is hydrogen, aliphatic group having 1 to 3 carbons, fluoro, chloro, bromo, iodo, nitro, cyano, hydrocarbonyl, alkylcarbonyloxy wherein alkyl can be C1–C6, alkoxycarbonyl wherein alkoxy can be C1–C6, hydroxycarbonyl, (C1–C8) alkoxy, (C1–C8) alkanoylamino, (C1–C5) alkylsulfonamido, hydroxy, amino which can be substituted with one or two (C1–C3) alkyl groups, aminocarbonyl that can be N-substituted with one or two (C1–C6) alkyl groups, (C1–C3) haloalkylsulfonamido, (C1–C3) haloalkyl, or alkanoylalkyl wherein alkanoyl is C2–C3 and alkyl is C1–C3 and the like;

(6) $R^4$ is an aliphatic group having 1 to 3 carbons, cyano, hydroxycarbonyl, hydroxycarbonyl, alkylcarbonyloxy wherein alkyl can be C1–C6, or alkoxycarbonyl wherein alkoxy can be C1–C6, and the like;

(7) $R^8$ and $R^9$ are independently hydrogen, aliphatic group having 1 to 3 carbons, fluoro, chloro, bromo, iodo, nitro, cyano, carboxyaldhyde, hydroxycarbonyl, alkylcarbonyloxy wherein alkyl can be C1–C6, alkoxycarbonyl wherein alkoxy can be C1–C6, (C1–C8) alkoxy, (C1–C8) alkanoylamino or (C1–C5) alkylsulfonamido, and the like;

(8) $R^6$ is a (C1–C6) aliphatic group, (C6–C 10) aryl, (C7–C10) aralkyl, or a (C1–C3) aliphatic group substituted with a 5 or 6-membered heteroaromatic ring having up to 4 heteroatoms comprising nitrogen, sulfur or oxygen atoms, and the like; and (9) $R^7$ is —O—$R^{10}$ or —O—(C=O)—$R^{11}$ where $R^{10}$ is a hydrogen or $R^{10}$ and $R^{11}$ are (9a) an aliphatic group with 1 to 6 carbons, which aliphatic group may be substituted with one to 3 of: hydroxy, fluoro, chloro, bromo, iodo, cyano, amino which can be substituted with one or two (C1–C3) alkyl groups, (C1–C6) alkanoylamino, hydroxycarbonyl, alkylcarbonyloxy wherein alkyl can be C1–C6, alkoxycarbonyl wherein alkoxy can be C1–C6, aminocarbonyl which can be N-substituted with one or two (C1–C6) alkyl groups, (C1–C5) alkylsulfonate which can be partially or fully halogenated wherein halo is fluoro, chloro, bromo or iodo, (C1–C3) alkoxy, nitro, (C1–C6) alkyl, (C1–C3) haloalkyl, alkanoylalkyl wherein alkanoyl is C2–C3 and alkyl is C1–C3, or hydrocarbonyl, and the like, and wherein the aliphatic group can be substituted with an aryl or heteroaryl group where the aryl or heteroaryl moiety comprises a 6 or 10-membered aromatic ring, of which up to 4 ring atoms can be nitrogen heteroatoms, (9a1) wherein the aryl or heteroaryl group can be substituted with up to 4 substituents selected from the group consisting of (C1–C3) aliphatic group, fluoro, chloro, nitro, cyano, carboxyaldhyde, carboxyl, alkylcarbonyloxy wherein alkyl can be C1–C6, alkoxycarbonyl wherein alkoxy can be C1–C6, aminocarbonyl which can be substituted with one or two (C1–C6) alkyl groups, amino, amino substituted with one or two (C1–C3) hydrocarbons, (C1–C6) alkanoylamino, hydroxy, (C1–C3) alkoxy, amino, (C1–C3) alkylsulfonate, (C1–C3) haloalkylsufonate, (C1–C3) haloalkyl, and alkanoylalkyl wherein alkanoyl is C2–C6 and alkyl is C1–C6, and the like, or (9b) an aryl or heteroaryl group where the aryl or heteroaryl group comprises a 6 or 10-membered aromatic ring, of which up to 4 ring atoms can be nitrogen, wherein the aryl or heteroaryl group can be substituted with up to 4 substituents selected from the group consisting of (C1–C3) alkyl, (C1–C3) alkenyl, fluoro, chloro, iodo, bromo, nitro, cyano, carboxyaldhyde, hydroxycarbonyl, alkylcarbonyloxy wherein alkyl can be C1–C6, alkoxycarbonyl wherein alkoxy can be C1–C6, aminocarbonyl which can be N-substituted with one or two (C1–C6) alkyl groups, amino, amino substituted with one or two (C1–C3) aliphatic groups, (C1–C6) alkanoylamino, carboxyl (C1–C6) ester, hydroxy, (C1–C3) alkoxy, (C1–C3) alkylsulfonamido, (C1–C3) haloalkylsulfonamido, (C1–C3) haloalkyl, or alkanoylalkyl wherein alkanoyl is C2–C3 and alkyl is C1–C3, and the like.

Preferably, in the method, when $R^7$ is acetyl the compound differs from chrysodin by at least one of (a) the presence or absence of a methylene, (b) the presence of sulfur or nitrogen in the compound in place of an oxygen, (c) the presence of halo, hydroxy, alkoxy, amino, nitro, alkanoylamino, aminocarbonyl, substituted aminocarbonyl, alkoxycarbonyl, hydroxycarbonyl, cyano, alkylsulfonamido, haloalkylsulfonamido, mono or dialkylamino, alkanoylalkyl or hydrocarbonyl or (d) the presence in $R^1$ or $R^7$ of a carbocyclic or heterocyclic ring.

Preferably, the aliphatic groups of compound I are alkyl. Preferably, the heterocyclic ring of $R^1$ is a heteroaryl moiety. Preferably the heteroaryl moiety of $R^1$ or $R^7$ is a pyridyl, thienyl, furanyl, pyrazinyl, pyrrolyl, indolyl, pyrimidyl, thiazolyl, isothiazolyl, oxazolyl, isoxazolyl, triazolyl, tetrazolyl, quinolyl or isoquinolyl. Preferably, the carbocyclic ring of $R^1$ is a aryl moiety, which is more preferably phenyl or naphthyl. Preferably, $R^7$ includes at least one hydroxy. Preferably, $R^{10}$ and $R^{11}$ are aliphatic groups having 1 to 3 carbons, which may be substituted as set forth above. Preferably, $R^{10}$ and $R^{11}$ are substituted with at least one hydroxy. Preferably, the aliphatic group of $R^1$ has from about 2 to about 6 carbons. Preferably, the halo substituents of compound I are fluoro. Preferably, $R^3$ and $R^5$ each represent a half bond that together forms a double bond, or $R^3$ is hydrogen and $R^5$ is hydrogen.

Preferably, the alkanoylamino groups referred to above are at least C2.

Preferably, the compounds conform to formula II:

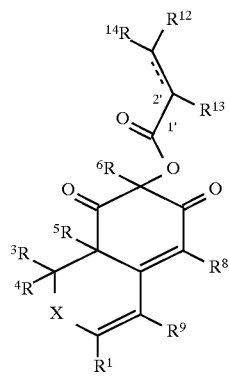

II wherein the bond indicated by the parallel solid and broken lines can be a single or double bond where, if a double bond, it can be a cis or trans double bond, wherein $R^{12}$ is aminocarbonyl which can be substituted with one or two (C1–C6) alkyl groups, hydroxycarbonyl, alkoxycarbonyl wherein alkoxy can be C1–C6, alkylcarbonyloxy wherein alkyl can be C1–C6, or trifluoromethanesulfate, $R^{13}$ is hydrogen or C1 to C3 alkyl, and $R^{14}$ is hydrogen, C1 to C3 alkyl, or hydroxy.

Preferably, the compounds conform to one of the following formulas:

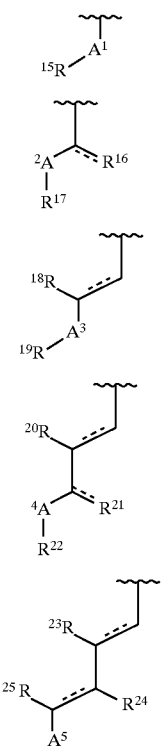

III

IV

V

VI

VII wherein the bonds represented with dashed lines are single or double bonds, $R^{15}$, $R^{17}$, $R^{19}$ and $R^{22}$ are (C1–C10) aliphatic groups, $R^{16}$, $R^{18}$, $R^{20}$, $R^{21}$, $R^{23}$, $R^{24}$ and $R^{25}$ are methyl, methylene or hydrogen, wherein $A^1$, $A^2$, $A^3$, $A^4$ and $A^5$ are six-membered aromatic or heterocyclic rings, having up to 4 nitrogen ring atoms and the rest carbon, $A^1$, $A^2$, $A^3$, $A^4$ and $A^5$ can be substituted with up to 4 substituents selected from the group consisting of fluoro, chloro, bromo, iodo, nitro, cyano, amino, (C1–C3) mono or di-alkylamino, (C1–C8) alkanoylamino, (C1–C3) alkylsulfonamido, (C1–C3) haloalkylsulfonamido which can be fully or partially halogenated wherein halo is fluoro, chloro, bromo or iodo, aminocarbonyl which can be substituted with one or two (C1–C6) alkyl groups, alkylcarbonyloxy wherein alkyl can be C1–C6, (C1–C6) alkoxycarbonyl, hydroxycarbonyl, (C1–C3) haloalkyl, which can be fully or partially halogenated wherein halo is fluoro, chloro, bromo or iodo, hydroxy, (C1–C8) alkoxy, and alkanoylalkyl wherein alkanoyl can be C2–C3 and alkyl can be C1–C3, and wherein the dashed lines indicate bonds that are either double or single bonds. Preferably $R^{15}$, $R^{17}$ $R^{19}$ and $R^{22}$ include an unsaturated bond conjugated to another unsaturated bond. Preferably, the illustrated two bonds linking $A^1$, $A^2$, $A^3$, and $A^4$ are meta to each other. Preferably, at least one of the dashed lines in each of formulas IIl-VII represents a double bond.

In the method of treatment, preferably the microbial infection is a fungal infection. Preferably, the fungal infection is caused by a fungus selected from the group consisting of fungi of the genus Candida, fungi of the genus Aspergillus, fungi of the genus Blastoschizomyces, fungi of the genus Cryptococcus, fungi of the genus Histoplasma, fungi of the genus Microsporum, fungi of the genus Sporothrix, fungi of the genus Torulopsis, fungi of the genus Trichophton, fungi of the genus Coccidioides such as *Coccidioides immitis*, fungi of the genus Epidermophyton such as *Epidermophyton floccosum* and fungi of the genus Mucor. More preferably, the fungal infection is caused by a fungus selected from the group consisting *Candida albicans, Candida tropicalis*, and *Mucor rouxii*. Also preferably, the fungal infection is caused by a fungus selected from the group consisting of fungi of the genus Candida, fungi of the genus Aspergillus, fungi of the genus Cryptococcus, fungi of the genus Histoplasma, fungi of the genus Trichophton, and fungi of the genus Mucor.

In the method of treating, preferably the infecting microbe expresses fatty acid synthetase and the animal is treated with a composition comprising an amount of a compound of formula I effective to inhibit the expressed fatty acid synthetase.

Preferably, the pharmaceutical composition comprises a pharmaceutically acceptable diluent or excipient, which can include liposomes containing the compound of formula I.

A method of treating a microbial disease comprising (a) combinatorially generating compounds by contacting a first compound according to formula I, excepting that $R^7$ is replaced by $R^{29}$, which differs from $R^7$ only in encompassing —OH, (i) with two or more second compounds that share a functionality that is expected to be reactive with the first compound or (ii) separately with two or more concentrations of a third compound having a functionality that is expected to be reactive with the first compound, (b) identifying among the generated compounds a selected compound or selected pool of compounds having relatively greater antimicrobial activity, and (c) administering the selected compound or pool to an animal to treat a microbial infection, wherein the contacting of step (a) occurs under conditions suitable for the reaction of the first compound with the reactive functionalities of the second or third compounds. Preferably, the second compounds are acylating agents. Alternatively, the second compounds are alkylating agents. In another alternative, the first compounds are according to formula VIII and the second compounds are amines. In another alternative, the first compound has a O at position 1 and the second compounds are O-alkylhydroxyamines. In another alternative, the first compound has a O at position 1 and the second compounds are carbazates which may be substituted. In another alternative, the third compound is hydrogen. Preferably, the method further comprises the step of assaying two or more pools of compounds for the ability to inhibit a microbial FAS, wherein each pool comprises one or more of the generated compounds from the contacting step.

For the purposes of this application, the fused ring structure shared by formulas I and II shall be referred to as the "AB ring", the individual rings referred to as the A and B rings, as indicated, and the ring positions shall be numbered as indicated.

DEFINITIONS

The following terms shall have the meaning set forth below:

antifungal agent
  an antimicrobial agent that acts on one or more strains of fungi.
antimicrobial agent
  a biological agent that inhibits the reproduction or decreases the survival of pathogenic microbial cells or inhibits the propagation, which includes without limitation replication, viral assembly or cellular infection, of a virus.
antimicrobial effective amount
  an amount of an antimicrobial agent administered to an animal infected with a microbe which is effective to reduce the rate at which the microbe reproduces or to reduce the population of the microbe in the organism.
biological agent
  an agent that is useful for diagnosing or imaging or that can act on a cell, organ or organism, including but not limited to drugs (pharmaceuticals) to create a change in the functioning of the cell, organ or organism.
FAS inhibiting effective amount
  an amount of an antimicrobial agent effective (a), for a systemic infection, to produce a blood concentration in the treated animal of the antimicrobial agent effective in vitro to create a statistically significant inhibition of the FAS of the infectious organism or (b), for nonsystemic infections, to produce a localized concentration of the antimicrobial agent effective in vitro to create a statistically significant inhibition of the FAS of the infectious organism. The in vitro assay used measures the synthesis of fatty acids at pH 6.6, at a temperature of 25° C., in the presence of 500 $\mu$M NADPH, 500 $\mu$M malonyl CoA, 20 $\mu$M acetyl CoA and appropriate buffers and salts.
microbe
  a bacteria, mycoplasma, fungi including but not limited to yeast, virus, protozoa or parasite (such as a malaria parasite).

DETAILED DESCRIPTION

Recent experiments that are described in Example 7 have now shown that the gene for FAS is important to the ability of Candida albicans to infect. This has been done by "knocking out" or rendering ineffective one or both alleles of the FAS gene of the CA14 strain of Candida albicans and comparing the ability of these derivative strains to the parent strain to establish an oral infection in Sprague-Dawley rats and a systemic infection in BALB/c mice. The experiments have shown that the parent strain and strains having one residual FAS allele remain able to establish an infection, while a strain in which both alleles have been knocked out is ineffective in producing an infection.

The invention provides a family of compounds according to the basic formula:

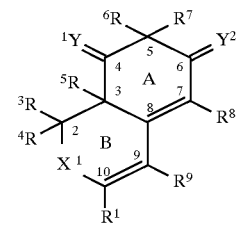

The substituents for this formula are as described above. The family includes the following compound A and compound B:

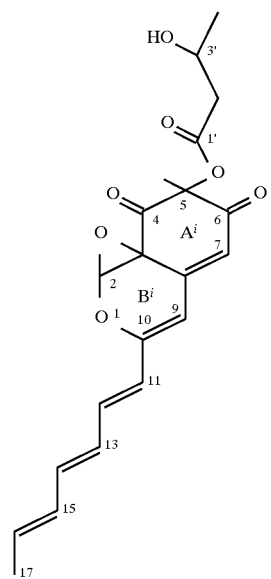

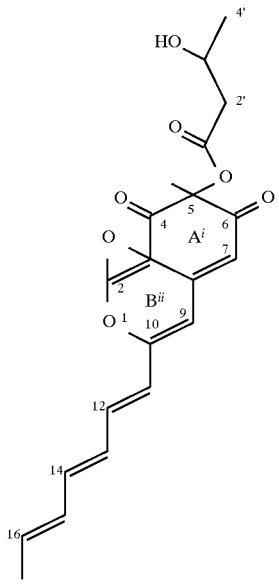

Compound A and Compound B have been isolated from a fungal cell line as described in Example 1. These compounds are useful as starting material to synthesize compounds within the above-described family of compounds of the invention.

Epoxides such as compound A can be deoxygenated for example to obtain compound B by a number of means known to the art, including treatment with the following deoxygenation reagents: (a) $WCl_6$ and n-BuLi; (b) $Ph_3P$; (c) $(EtO)_3P$; or (d) $H_2NCSNH_2$.

The acyl substituent at the 5 position of the $A^i$ ring can be removed by several methods known to the art including (1) treatment a strong base such as a metal alkoxide in an alcoholic solvent or, in the case of compound B, (2) oxidation of the exposed alcohol functionality at the 3' position to a ketone, for instance using a mixture of oxalyl chloride, dimethylsulfoxide (DMSO) and triethylamine, followed by reaction with phenyl hydrazine. The thus exposed hydroxyl group at the 5 position can then be acylated or alkylated by known means.

Note, that the discussion herein focuses on compound A or compound B as a model for describing chemical protocols. Those of ordinary skill in the art will recognize that these protocols are applicable to others of the compounds within the genus described above.

When the hydroxyl at the 3' position of compound B is oxidized to a ketone, this ketone can be reacted with triflic anhydride ($Tf_2O$) or N-phenyl triflamide (PhNHTf) in a mixture of an aprotic solvent and a base such as pyridine or triethylamine to form a —O—CO—C=C(OTf)($CH_3$) structure at the 5 position of the $A^i$ ring. The compound containing this —O—CO—C=C(OTf)($CH_3$) structure can be reacted in an alcoholic solvent or in a mixture of a solvent alcohol (ROH) and a dipolar, aprotic solvent such as dimethyl formamide (DMF) with carbonmonoxide and catalytic amounts of palladium salts in the presence of 1,3-bis (diphenylphosphinopropane) to convert the structure to —O—CO—C=C(COOR)($CH_3$), where R is from the solvent alcohol ROH. The ester function of the —O—CO—C=C($CO_2R$)($CH_3$) structure can be hydrolyzed by known methods to create a carboxylic acid that can serve as starting material for additional side chain modifications. For instance, the acid functionality can be reacted, using a condensation reagent such a dicyclohexyl carbodiimide, with an amine compound to form an amide. Such amine compounds can, of course, carry additional functionalities, such as protected carboxylic acid moieties.

The substituent at the 5 position of the $A^i$ ring of the B compound can be converted to a —O—CO—CH=CH—$CH_3$ by reacting the B compound with methane sulfonyl chloride in a solvent containing base.

The oxygen of the $B^{ii}$ ring of compound B can be substituted with an amine nitrogen by reacting compound B with an an amine compound, such as without limitation, alkyl amine, O-alkylhydroxyamine, an amino acid, and t-butylcarbazate. The alkyl amine, alkylhydroxyamine and t-butylcarbazate ($NH_2NHCO_2$-tBu) reactions form the following compounds, respectively:

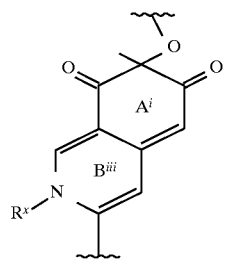

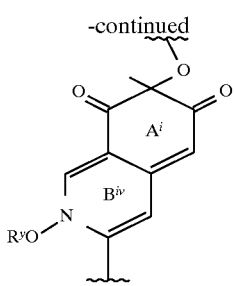

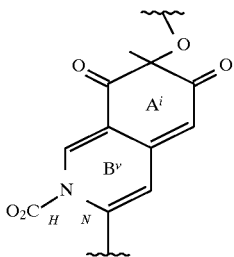

The $CO_2$ moiety of formula 3 can be removed with acid, exposing a hydrazine functionality that can be used to attach electrophilic reagents such as acid chlorides.

The oxygen of the $B^{ii}$ ring of compound B can be converted to a sulfur by reaction with sodium sulfide under strongly basic conditions, for example in the presence of potassium t-butoxide. The carbonyls at positions 4 and 6 of compound B can be converted to the corresponding thiocarbonyls by reaction in an inert solvent with Lawesson's reagent according to standard procedures. The $A^i$ or the $B^{ii}$ rings of compound B can be substituted for instance by reaction with a mixture of DMF and phosphorous oxychloride under standard Vilsmeier conditions, or with preformed N,N-dimethylchloroiminium chloride in a suitable solvent.

The 5-position of the A ring can define a chiral center. Both stereoisomeric forms of this chiral center are within the invention. When an epoxide is formed between the 2 and 3-position of the B ring, two stereoisomeric forms are possible; both such forms are within the invention.

The compounds of the invention provide useful starting points for combinatorial chemistry approaches to identifying particularly effective antimicrobial compounds which are then used to treat infections. The most common combinatorial approach creates numerous pools of related compounds, where each pool contains a different set of such compounds. Typically, the pools are created by reaction schemes that yield multiple related compounds. The pools are assayed for a useful characteristic and pools containing compounds with this characteristic are identified. The known information on the contents of these pools is then used to either prepare a library of potentially useful compounds or to design more focused combinatorial pools of compounds. The library of compounds or the new combinatorial pools are then tested for the useful characteristic. Eventually, by this process of elimination specific compounds having the useful characteristic are identified.

For one example of the combinatorial approach, the compounds defined by the formula 4 below can be reacted with mixtures of various acyl chlorides to create pools of compounds having different acyl groups at the 5 position of the $A^{ii}$ ring.

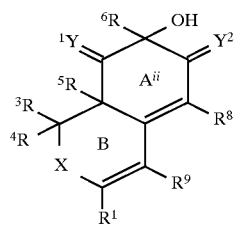

Examples of the acyl chlorides that can be used include without limitation acetyl chloride, benzoyl chloride, halo-acetyl chloride, halo-benzoyl chloride, phenylacetyl chloride, 3-cyclohexylpropanoyl chloride, isovaleryl chloride, 2-napthoylacetyl chloride, 6-phenylhexanoyl chloride, and 3-fluoropropionyl chloride. These pool-forming reactions could, for instance, be conducted in THF with 1.0 mmol of compound 4, 1.1 mmol pyridine and 0.1 mmol of each of a number (e.g., 10) of acyl chlorides. The reaction mixtures can further include 4-dimethylaminopyridine (e.g., 0.1 to 1.0 mmol) as a catalyst.

Alternatively, the compounds of formula 4 can be reacted with alkylating reagents in the presence of a strong proton extraction agent such as potassium t-butoxide to form compounds having various ether attachments at the 5 position of the $A^{ii}$ ring. Examples of such alkylating reagents include without limitation methyl iodide, ethyl triflate, propyl mesylate, phenethyl iodide, 4-cyclohexylbutyl triflate, 3-methylbenzyl bromide, 4-methoxybenzyl bromide, chloromethyl methyl ether, 4-methoxybutanyl triflate and isopropyl triflate.

In another example of a combinatorial approach, mixtures of amine compounds are reacted with compounds of formula 5 illustrated below, to substitute amine or substituted amines at the position of the ring oxygen.

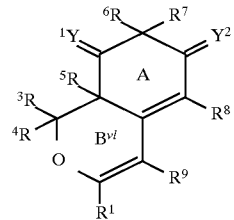

Examples of such amines include without limitation ammonia, methylamine, 20 n-propylamine, cyclohexylmethylamine, benzylamine, 4-chlorobenzylamine, 3-trifluoromethylphenethyl amine, 4-phenylbenzylamine, phenethylamine and sec-pentylamine.

Another combinatorial approach would take compounds of the invention and hydrogenate in the presence of, for instance, a palladium, platinum, rhodium or nickel catalyst using various ratios of hydrogen gas designed to eliminate various numbers of double bonds.

The antimicrobial agent of the invention can be administered orally, ocularly, topically, rectally, vaginally, by pulmonary route by use of an aerosol, or parenterally, i.e. intramuscularly, subcutaneously, intraperitoneallly or intravenously. The antimicrobial agent of the invention can be administered alone, or it can be combined with a pharmaceutically-acceptable carrier or excipient according to standard pharmaceutical practice. For the oral mode of administration, the antimicrobial agent can be used in the form of tablets, capsules, lozenges, troches, powders, syrups, elixirs, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the antimicrobial agent can be combined with emulsifying and suspending agents. If desired, certain sweetening and/or flavoring agents can be added. For parenteral administration, sterile solutions of the antimicrobial agent are usually prepared, and the pH of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchronium chloride, and the usual quantities of diluents and/or carriers. For pulmonary administration, diluents and/or carriers will be selected to be appropriate to allow the formation of an aerosol. For parenteral administrations, particularly intravenous administrations, liposomal formulations can be used. Such liposomal formulations are particularly preferred for the more hydrophobic antimicrobial compounds of the invention.

Experiments described below in Example 1 have shown that compound B is not directly inhibitory of FAS using the in vitro assay described below. However, cell extracts made after exposure to compound B have markedly reduced FAS activity. Without limiting the invention to theory, it is believed that compound B is metabolized to a form that inhibits FAS.

The antimicrobial agents of the invention are suitable for use in animals including mammals such as humans.

A number of compounds either are not within the invention, are not within certain embodiments of the invention or are preferably excluded. These compounds are:

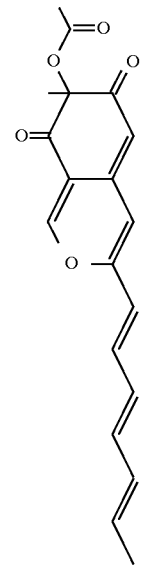

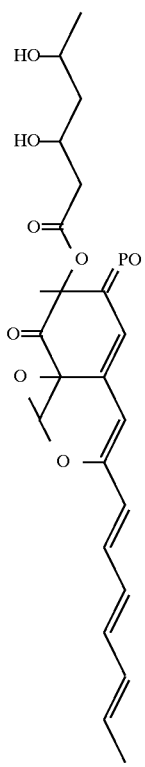

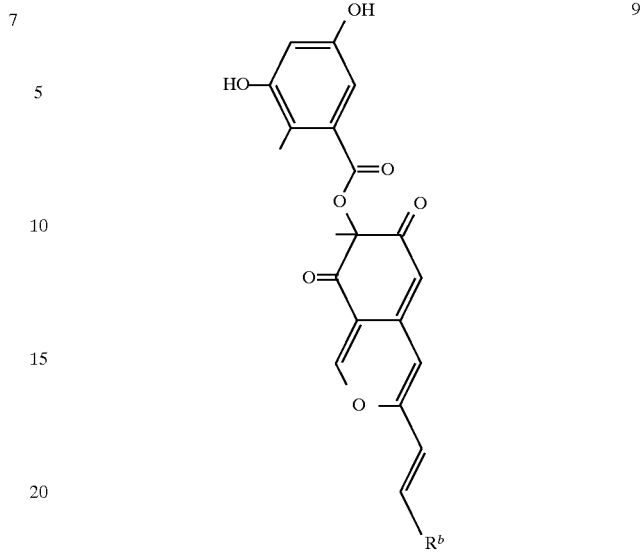

In the above formulas, $R^a$ represents hydrogen, acetyl, 2-methyl-3,5-dihydroxy-phenylcarbonyl or methyl, Z represents oxygen or NH, and $R^b$ is methyl, hydroxymethyl or carboxyl. Formula 7 describes chrysodin. Formula 8 describes patulodin. Formula 9 describes sclerotiorin and related compounds. Formula 10 describes mitorubicin and related compounds. Preferably, when $R^7$ of formula I is acetyl the compound of the invention differs from chrysodin by at least one of (1a) the presence or absence of a methylene, (1b) the presence of sulfur or nitrogen in the compound in place of an oxygen, (1c) the presence of halo, hydroxyl, alkoxyl, amino, nitro, alkanoylamino, aminocarbonyl, substituted aminocarbonyl, alkoxycarbonyl, carboxylate, cyano, alkylsulfonamido, haloalkylsulfonamido, alkylamino, alkanoylalkyl or carboxyaldehyde or (1d) the presence in $R^1$ or $R^7$ of a carbocyclic or heterocyclic ring. Preferably, when $R^7$ is 2,4-dihydroxypentyl the compound of the invention differs from patulodin by at least one of (2a) the presence or absence of a methylene, (2b) the presence of sulfur or nitrogen in the compound in place of an oxygen, (2c) the presence of halo, hydroxyl, alkoxyl, amino, nitro, alkanoylamino, aminocarbonyl, substituted aminocarbonyl, alkoxycarbonyl, carboxylate, cyano, alkylsulfonamido, haloalkylsulfonamido, alkylamino, alkanoylalkyl or carboxyaldehyde, (2d) the presence in $R^1$ or $R^7$ of a carbocyclic or heterocyclic ring or (2e) the absence of an epoxide moiety. Preferably, the difference recited in (1 a) and (2a) is at least two methylenes. Preferably, either the 7-position of the A ring is not substituted with chloro or the $R^1$ position differs from a 3,5-dimethyl-hepta-1,3-dienyl group. Preferably, $R^7$ is either (a) not one of 2-methyl-3,5-dihydroxy-phenylcarbonyl or methyl or (b) $R^1$ is not one of propyl-2-enyl, 1-hydroxypropyl-2-enyl or 1-carboxyl-ethylenyl.

The invention is further explained by reference to the following non-limiting examples.

EXAMPLE 1—ISOLATION OF COMPOUND A AND COMPOUND B

Example 1A—Isolation Procedures

An inoculant of microorganism CK2108, which is a *Penicillium solitum* Westling fungus deposited with the American Type Cutlture Collection in a deposit pursuant to the Budapest Treaty under Accession No. 74361 was fermented in 25 mls of a seed broth at 28° C. for two days. Each 1 L of the seed broth was formulated as follows:

| | |
|---|---|
| Glucose | 20.0 g |
| PHARMAMEDIA | 15.0 g |
| (Traders Oil Mill Co., Ft. Worth, TX) | |
| $(NH_4)_2SO_4$ | 3.0 g |
| $ZnSO_4 \cdot 7H_2O$ | 0.03 g |
| $CaCO_3$ | 4.0 g |
| Yeast extract | 5.0 g |
| $H_2O$ | to 1 L |

The overnight inoculant was used to inoculate 3 liter of broth according to the following formula:

| | |
|---|---|
| Glucose | 20.0 g |
| Sucrose | 50.0 g |
| PHARMAMEDIA | 20.0 g |
| (Traders Oil Mill Co., Ft. Worth, TX) | |
| $NaNO_3$ | 1.0 g |
| $K_2PO_4$ | 0.5 g |
| KCl | 0.7 g |
| L-histidine | 1.0 g |
| $MgSO_4 \cdot 7H_2O$ | 0.014 g |
| $H_2O$ | to 1 L |

The 3-liter culture was fermented for 5 days at 28° C. The fermentation was then extracted with 7.5 liters of ethyl acetate. The organic extract was dried to yield 12.36 g of crude extract.

400 mg of crude extract was processed using a coil planet centrifuge ("CPC"), an apparatus for conducting counter-current chromatography ("CCC") marketed by P.C. Inc. of Potomac, Md. Two solvent phases were formed from 1:4:4:4 of n-hexane: ethyl acetate: methanol: water. 400 mls of the lower phase were loaded into the coil of the CPC to form the stationary phase. The extract was mixed with 9 mls of the two-phase mixture of solvents and the soluble components (217 mg) were injected into the CPC. The coil was then rotated to hold the stationary phase in place while the upper phase solvent was pumped through the coil at 3 ml/min. Elution was monitored by absorbance at 270 nm. Two major peaks, a first eluting peak (48 mg) and second eluting peak (10 mg), were observed. The first eluting peak had activity as tested by the MIC assay of Example 1B; the second eluting peak was more active on a weight basis than the first. The first eluting peak also had activity in the enzyme inhibition assay of Example 1C.

The two components were separately fractionated using reverse-phase liquid chromatography on a 10×250 mm C18 column from Merck (Darmstadt, Germany). The flow rate used was 10 ml/min. The solvent program started with 70% water, 30% acetonitrile. A 25 minute linear gradient to 100% acetonitrile was initiated at injection. The sample (5 mg) was injected in 50 µl DMSO. Fractions were collected each ½ minute. Elution was monitored by absorbance at 270 nm. The material from the first eluting peak from the CPC displayed one major peak that eluted in fractions 25–27. This material "compound A" retained activity in the MIC assay of Example 1B and the enzyme inhibition assay of Example 1C. The material from the second eluting peak from the CPC displayed one major peak that eluted in fraction 23. This material "compound B" retained activity in the MIC assay of Example 1B.

NMR analysis such as that described in Example 1D, suggested the insoluble material from the CPC separation was substantially compound A.

Example 1B—MIC assay

The fractions from the purification were tested for antifungal activity against *C. albicans* (strain B311A available from Dr. Paul Actor, Temple University and strains ATCC Nos. 10231 and 10261) and *C. tropicalis* (strain 13803). Fungi were grown in 1× yeast nitrogen broth ("YNB") medium (BBL, Cockeysville, Md.) containing 15 µg/ml aspargine and 100 µg/ml kanamycin. Prior to the assay for antifungal activity, the fungus to be tested for susceptibility was grown overnight from a single colony in 5 ml of medium at 30° C. This overnight culture was diluted 1:10 with fresh medium and grown at 37° C. for 4 hours. A volume of 5 µl of extracts, dissolved in DMSO, was added to each separate well in a series of 96-well plates. 4,000 fungal cells were then added to each plate in 95 µl of medium. The optical densities of the wells were measured and the plates incubated at 37° C. The optical densities were again measured after 24 and 48 hours. Minimum inhibitory concentrations ("MICs") for the extracts were determined using this procedure wherein the extracts were serially diluted in medium prior to mixing with the 4,000 fungal cells.

Using the procedure described in the previous paragraph, it was determined that the MICs for compound A and compound B against *Candida Albicans* strain B311A grown in YNB medium were 25 µg/ml and 6.25 µg/ml, respectively. When Sabouraud Dextrose Broth (Difco, Detroit, Mich.) was substituted for YNB medium, the MIC value for each compound was 50 µg/ml.

Example 1C—FAS inhibition assay

To test the compounds for FAS inhibitory activity, an FAS extract from *Saccharomyces cerviseae* was prepared. Freeze dried yeast (Fleishmans' freeze dried yeast, Specialty Brands, San Francisco, Calif.) 1 g, was hydrated in 5 mls deionized water for 15 minutes at 4° C. Subsequent extraction steps were conducted at a temperature between 4° C. and 10° C., except that in the cell lysis step the temperature may have briefly exceeded these boundaries. The cells were pelleted by centrifugation; the pelleted volume was measured; and the cells were resuspended in 5 vol. (5 mls per ml cell volume) extraction buffer [125 mM KH2PO4, pH 6.6, 1 mM EDTA, 1 mM DTT, 0.7 µg/ml pepstatin (Boehringer Mannheim, Indianapolis, Ind.), 0.2 µg/ml aprotinin (Boehringer Mannheim, Indianapolis, Ind.), 0.2 μg/ml leupeptin (Boehringer Mannheim, Indianapolis, Ind.)]. The cells were again pelleted and resuspended in 2 vol. extraction buffer. The cells were lysed using a bead mill homogenizer (Biospec Products, Bartlesville, OD) with a volume of glass beads equal to the volume of the yeast cells. The bead mill was operated five times for 1 minute, with 1 minute intervals between operations to allow the water jacket of the bead mill to cool the material in the mill. The lysate was centrifuged at 30,000×g for 30 minutes and the supernate was collected. Ammonium sulfate was added to the supernate to 50% saturation and the mixture was stirred for 30 minutes on ice. The precipitate was collected by centrifugation (10,000×g, 10 min) and dialyzed against three changes of dialysis buffer (125 mM $KH_2PO_4$, pH 6.6, 1 mM EDTA, 1 mM DTT, 3 mM sodium azide) and the dialyzed material collected as the "FAS extract."

105 μl of FAS extract was placed in each well of a polypropylene 96 well plate (Costar Corp. Cambridge, Mass.) and multiple 5 μl dilutions of compound A, compound B or negative control solution were introduced into each of the wells. Following this, the plate was incubated at room temperature for 30 minutes. Duplicate alloquots of 50 μl from each well were transferred into separate wells of a 96-well PolySorp micotiter plate (Nunc, Denmark). Into each well of the PolySorp plate, were added simultaneously 50 μl of freshly prepared 2× assay cocktail (a mix of: 833 μl 3M $K_2HPO_4$, pH 6.6; 1 ml 10 mM NADPH (Sigma Chemical Co., St. Louis); 1 ml 10 mM malonyl-CoA (Sigma); 40 μl 10 mM acetyl-CoA (Sigma); 20 μl 1M DTT (Sigma); 7.1 ml deionized water). The relative initial reaction rates in each well were measured by measuring the decrease in optical density at 340 nm using a UV Max microtiter plate reader (Molecular Devices, Sunnyvalle, Calif.).

Using the above-described method, compound A was found to inhibit FAS from *S. cereviseae* with an $IC_{50}$ of 160 μg/ml.

Example 1D—Structural Analysis

Mass spectroscopy determined that compound A had a molecular formula of $C_{21}H_{22}O_7$ and compound had a molecular formula of $C_{21}H_{22}O_6$. Compound B was analyzed by a homonuclear ($^1H$—$^1H$) COSY 2-D NMR experiment. The COSY data indicated a spin system having three trans double bonds (C11–C17) and another comprising a hydroxypropyl group (C2'–C4'). A heteronuclear multiple quantum coherence experiment was used to align the hydrogen atoms indicated by $^1H$-NMR with carbon atoms indicated by $^{13}C$-NMR. The combined NMR data implied the structure indicated above in the Detailed Description. Once this structural determination was made, it was quickly determined that the NMR data for compound A implied the structure indicated above in the Detailed Description.

Compound A showed 1H-NMR and $^{13}C$-NMR spectra having peaks as indicated in the Table below. It is believed that the peaks can be assigned to particular carbons or to hydrogens attached to particular carbons as indicated in the Table.

| C/H # | $^1H$ | $^{13}C$ |
|---|---|---|
| 2 | 5.89 s | 82.07 |
| 3 | — | 55.54 |
| 4 | — | 197.39 |
| 5 | — | 85.84 |

-continued

| C/H # | $^1H$ | $^{13}C$ |
|---|---|---|
| 5-$CH_3$ | 1.62 s | 22.21 |
| 6 | — | 192.51 |
| 7 | 6.28 m | 120.71 |
| 8 | — | 146.71 |
| 9 | 6.11 s | 105.37 |
| 10 | — | 154.49 |
| 11 | 6.19 d, J = 15.2 | 123.77 |
| 12 | 6.95 dd, J = 15.1, 11.3 | 136.68 |
| 13 | 6.31 dd, J = 14.9, 11.4 | 129.93 |
| 14 | 6.56 dd, J = 14.8, 10.8 | 139.82 |
| 15 | 6.22 m | 132.6 |
| 16 | 5.94 m | 134.52 |
| 17 | 1.79 dd, J = 6.7, 0.6 | 18.57 |
| 1' | — | 171.09 |
| 2' | 2.52 dd, J = 14.3, 7.0<br>2.42 dd, J = 14.4, 6.0 | 43.17 |
| 3' | 4.11 m | 64.92 |
| 4' | 1.20 d, J = 6.2 | 23.21 |

EXAMPLE 2—DISK DIFFUSION ASSAY FOR ANTIMICROBIAL ACTIVITY

Fungal cells were grown overnight from a single colony in 2–5 ml Sabouraud Dextrose Broth at 37° C. 1–5×10$^6$ were spread onto Sabouraud Dextrose Agar plates (Difco, Detroit, Mich.). Sterile 6 mm filter disks were evenly spaced with at least about 22 mm separation on the plates. To each disk, 100 μg of a compound to be tested was applied in 5–10 μl DMSO. On each plate, two disks containing 2.5 and 10 μg, respectively, of Amphotericin B (Sigma) and two disks containing 2.5 and 10 μg, respectively, of cerulenin (Sigma) were used as positive controls. A disk containing only DMSO served as the negative control. The plates were incubated at 37° C. for 24 hours and the zone of growth inhibition about each disk was visually examined and measured. Compound A and compound B typically produced clear zones of 8–12 mm diameter. Amphotericin B typically produced a clear zone of 8–10 mm diameter. Cerulenin typically produced a hazy zone of 20–25 mm diameter. A clear zone is indicative of fungicidal activity, while a hazy zone is indicative of fungistatic activity.

By this method, compound A and compound B had antimicrobial activity against *Candida albicans* (strains ATCC 10231 and ATCC 10261) and *Candida tropicalis* (strain ATCC 13803).

EXAMPLE 3—IN VIVO ACTIVITY OF COMPOUND A AND COMPOUND B

In vivo activity was determined using a murine systemic model of candidiasis. Groups of 5 to 10 mice were inoculated IV with 1–2×10$^7$ cells of *C. albicans* strain ATCC 10231 (10 times the lethal dose). One hour after inoculation, the candidate antifungal compounds were delivered IP. 10 mg/kg of compound A was injected into each mouse of the compound A treatment group. Two separate treatment groups received 30 and 100 mg/kg, respectively, of compound B. Amphotericin B was injected into a positive control treatment group at 10 mg/kg. All compounds were delivered in phosphate-buffered saline (PBS) and one treatment group received PBS. Twice daily thereafter the mice were observed, the number of dead mice recorded, and the dead mice removed. After nine days, the total mortality over the period was determined.

Using the same methodology, it was determined that the maximal tolerated dose in these mice (i.e., the maximum dose that caused no deaths within 72 hours following IP administration) of compound B was in excess of 200 mg/kg. The mice treated with 2108B or Amphotericin B injected IP in 20 ml of phosphate buffered saline, pH 7.4 had the following treatment profiles:

| treatment compound | Dose mg/kg | \multicolumn{10}{c}{Deaths Each Day Post Inoculation} | % Survival |
|---|---|---|---|---|---|---|---|---|---|---|---|---|
| | | 0 | 1 | 2 | 3 | 4 | 5 | 6 | 7 | 8 | 9 | |
| vehicle | — | 0 | 1 | 1 | 0 | 1 | 1 | 1 | 0 | 0 | 0 | 0 |
| Compound B | 100 | 0 | 2 | 0 | 0 | 0 | 0 | 0 | 0 | 1 | 0 | 40 |
| Compound B | 30 | 0 | 2 | 1 | 0 | 0 | 0 | 0 | 0 | 0 | 0 | 40 |
| Amphotericin B | 10 | 0 | 0 | 0 | 0 | 1 | 0 | 0 | 0 | 0 | 0 | 80 |

Using the methodology described above, the maximum tolerated dose for compound A was 10 mg/kg. As indicated by the results below, this particular compound is more suitable for treating non-systemic infections in mice due to the low maximum tolerated dose.

| treatment compound | Dose mg/kg | \multicolumn{10}{c}{Deaths Each Day Post Inoculation} | % Survival |
|---|---|---|---|---|---|---|---|---|---|---|---|---|
| | | 0 | 1 | 2 | 3 | 4 | 5 | 6 | 7 | 8 | 9 | |
| vehicle | — | 0 | 0 | 0 | 3 | 0 | 0 | 2 | 0 | 0 | 0 | 0 |
| Compound A | 10 | 0 | 0 | 2 | 3 | 0 | 0 | 0 | 0 | 0 | 0 | 0 |
| Amphotericin B | 10 | 0 | 0 | 1 | 0 | 0 | 0 | 0 | 0 | 0 | 0 | 80 |

EXAMPLE 4—COMPARATIVE RESULTS

Strain 2108 was also determined to produce patulodin, as determined by NMR and mass spectroscopy. The structure of patulodin is as follows:

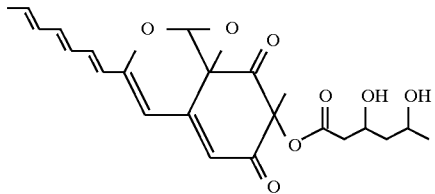

Using the test for antifungal activity set forth in Example 1B, the MIC for this compound against *Candida albicans* B311A was determined to be in excess of 100 µg/ml, which value is substantially higher than the values of 25 µg/ml and 6.25 µg/ml determined for compound A and compound B, respectively. Additionally, in the disk diffusion assay of Example 2, the zone of inhibition was 7 mm, barely larger than the disk itself.

EXAMPLE 5—CONVERSION OF COMPOUND A TO COMPOUND B

A dry 250 ml round bottom flask was flushed with nitrogen, charged with 60 ml of dry THF, and cooled to −78° C. Tungsten hexachloride 2.27 g, 5.74 mmol) was introduced into the flask. While the cold suspension was stirred, 7.18 ml (11.48 mmol) of 1.6M n-BuLi in hexane was added slowly. The resulting mixture was warmed to room temperature over two hours. The mixture was recooled to −78° C. and compound A (1.09 g, 2.82 mmol) was introduced. The cooling bath was removed and the mixture was stirred for 45 minutes and then poured into an aqueous sodium tartrate solution (prepared by dissolving 4.5 g, 30 mmol, of tartaric acid in 20 ml of 2N aqueous NaOH). This mixture was transferred to a separatory funnel, to which ethyl acetate (300 ml) and water (100 ml) were also added. The aqueous layer was extracted with additional ethyl acetate (2×100 ml) and the combined organic layers were washed with a brine solution (100 ml) made basic with 50 ml of 2N NaOH. The organic layer was dried over $MgSO_4$, filtered and evaporated to give a brown viscous oil. This material was purified by column chromatography on 64 g of silica gel, which was eluted with 65% ethyl acetate, 34% hexane, and 1% methanol. A small amount of nonpolar material eluted first followed by a fraction corresponding to starting material (85 mg) and finally the desired product (279 mg).

The compound B prepared by this process had the same physical properties, in terms of TLC $R_f$, HPLC retention time, UV spectra, $^1H$ NMR spectra and mass spectra, as the natural product. The HPLC protocol used a 10×100 mm $C_{18}$ reversed-phase column from Merck (Darmstadt, Germany). The column was equilibrated with 95% $H_2O$, 5% $CH_3CN$ and developed with a 25 minute linear gradient to 100% $CH_3CN$. The mass spectra showed major ion peaks at 393.4 ($M+Na^+$), 371.4($M+H^+$), 198.3 and 166.3 m/e.

EXAMPLE 6—ADDITIONAL CONVERSIONS OF COMPOUND A TO COMPOUND B

Reaction A. Compound A was converted to compound B using $WCl_6/2$ n-BuLi according to the method of Umbreit and Sharpless, *Organic Synthesis Coll. Vol. VII*, p. 121. A dry 25 mL round bottom flask was flushed with nitrogen, charged with dry THF (4.0 mL), and cooled to −78° C. Tungsten hexachloride (148 mg, 0.37 mmol) was introduced. While the cold suspension was stirred, 1.6M n-BuLi in hexane (0.46 mL, 0.74 mmol) was added slowly. The resulting mixture was stirred for 0.5 hour before warming to room temperature for 0.5 hour. The mixture was recooled to −78° C. and compound A (77 mg, 0.20 mmol) was introduced. The cooling bath was removed and the mixture was stirred for 90 minutes and then poured into a separatory funnel containing a saturated aqueous potassium sodium tartrate solution (20 mL) made basic with 2M NaOH (20 mL). This mixture was extracted with chloroform (3×25 mL). The combined organic layers were washed with a brine solution (100 mL) and dried over $MgSO_4$. After filtration, rotary evaporation afforded a brown viscous oil.

For this reaction and reactions B, C and D, described below, product was isolated by reversed-phase HPLC on a Merck 10×250 mm $C_{18}$ column (Darmstadt, Germany). The column was equilibrated with 95% $H_2O$, 5% $CH_3CN$ and developed with a 25 minute linear gradient to 100% $CH_3CN$. Mass Spectroscopic analysis of the product eluting at between 13 and 15 minutes confirmed the presence of compound B.

Reaction B. Compound A was converted to compound B using $Ph_3P$ according to the method of Yamada et al., *J. Org. Chem.* 43:2076, 1976. A dry 25 mL round bottom flask was flushed with nitrogen, charged with compound A (77 mg, 0.2 mmol), dry benzene (5.0 mL), and triphenylphosphine (53 mg, 0.2 mmol). The resulting solution was warmed to reflux and stirred overnight. The reaction mixture was cooled, and solvent was removed by rotary evaporation leaving a brown viscous oil. Mass Spectroscopic analysis of the product eluting from the reversed-phase HPLC column at between 13 and 15 minutes confirmed the presence of compound B.

Reaction C. Compound A was converted to compound B using $(EtO)_3P$ according to the method of Scott, *J. Org. Chem.*, 22: 1118, 1957. A dry 25 mL round bottom flask was flushed with nitrogen, charged with compound A (77 mg, 0.2 mmol), dry benzene (5.0 mL), and triethyl phosphite (34 uL, 0.2 mmol). The resulting solution was warmed to reflux and stirred overnight. The reaction mixture was cooled, and solvent was removed by rotary evaporation leaving a brown viscous oil. Mass Spectroscopic analysis of the product eluting from the reversed-phase HPLC column at between 13 and 15 minutes confirmed the presence of compound B.

Reaction D. Compound A was converted to compound B using $H_2NCSNH_2$, $NaHCO_3$ and $Ph_3P$ according to the method of Goldbach, et al., *J. Chem. Soc. Chem. Comm.* 1987, pp. 1434 et seq. A dry 25 mL round bottom flask was flushed with nitrogen, charged with compound A (77 mg, 0.2 mmol), dry benzene (5.0 mL), sodium bicarbonate (25 mg 0.3 mmol), thiourea (15 mg, 0.2 mmol), and triphenylphosphine (53 mg, 0.2 mmol). The reaction was stirred at room temperature overnight. The reaction was quenched with water (20 mL) and extracted into ethyl acetate (3×25 mL). The combined organic layers were washed with a brine solution (10 mL) and dried over $MgSO_4$. After filtration, rotary evaporation afforded a brown viscous oil. Mass Spectroscopic analysis of the product eluting from the reversed-phase HPLC column at between 13 and 15 minutes confirmed the presence of compound B.

EXAMPLE 7—INFECTIVENESS OF *C. albicans* STRAINS LACKING THE FAS GENE

Example 7A—Description of the *C. albicans* Strains

To test whether the FAS is necessary to fungal infection, a number of *C. albicans* strains were developed. These had the following characteristics:

| Strain | Characteristics |
|---|---|
| SC5214 | The parent to the strains described below. Described in Fonzi and Irwin, Genetics 134: 717–728, 1993. This strain is virulent. Cole et al., FEMS Microbiol. Letts. 126: 177–180, 1995; Meitner et al., Infect. Immuno. 58: 228–2236, 1990. |
| CA14 | A URA3 double mutant. Described in Fonzi and Irwin, Genetics 134: 717–728, 1993. |
| CFD1 | A derivative of CA14 that is $Ura^+$ where a single FAS2 allele has been disrupted. The strain expresses 80% of the FAS activity of CA14. |
| CFD2 | A derivative of CA14 that is $Ura^+$ where one FAS2 allele has been deleted and the other disrupted. The strain expresses no detectable FAS. |
| CFD3 | A derivative of CFD2 where one FAS2 allele has been restored. The strain expresses 80% of the FAS activity of CA14. |

The methods used to make these derivative strains are described in Fonzi and Irwin, cited above. FAS2 sequences used were selected from the sequences identified in Southard and Cihlar, *Gene* 156: 133–138 and correspond to the condensation reaction domain.

Example 7B—Oral Candidiasis

Pathogen-free Sprague-Dawley rats (Charles River Labs, Inc., Kingston, N.Y.), 19–21 days of age, were screened for *C. albicans* by plating oral swabs onto YEPD and Sabouraud agar. *C. albicans*-free animals were operated upon to remove the salivary gland as described by Bowen et al., *Infect. Immunol.* 58: 2228–2236, 1990. Rats were divided into separate treatment groups. As appropriate for its treatment group, each rat was inoculated orally with a cotton-tipped applicator saturated with $10^6$ CFU of one of the *C. albicans* strains. After inoculation, the rats were caged individually to prevent cross-contamination and minimize coprophagy. At 7 days, the rats were sacrificed and the mandible hemisected and aseptically removed to 5 ml PBS. Adherent organisms were dislodged by sonication and plated, after serial dilution, onto the Sabouraud and YEPD plates, each plate supplemented with 1% Tween 40, 0.01% myristic acid and 0.10% stearic acid.

From the mandible extraction, the results were:

| strain | result (mean colonization) |
|---|---|
| SC5314 | $1.6 \times 10^5$ cfu |
| CDF1 | $2.8 \times 10^4$ cfu |
| CDF3 | $2.5 \times 10^4$ cfu |
| CDF2 | 410 cfu (no colonization for 3 of 5 animals). |

From these results it is clear that an internal mechanism for synthesizing fatty acids is essential to oral candidiasis.

Example 7C—Systemic Candidiasis

The requirement for FAS for virulence was also tested in the murine model developed by Bulaw et al., *Proc. Natl. Acad. Sci. USA* 92:10570–10574, 1995. BALB/c mice were divided into experimental groups of 10. Each animal in a group was inoculated via the lateral tail vein with a given strain at a given inoculum size. Morbidity and mortality were observed for a three week period. Animals exhibiting severe morbidity were sacrificed immediately.

At eleven days post-inoculation, all animals infected with $10^6$ cfu of SC5314, CFD1 and CFD3 were dead. All animals infected with $10^7$ cfu (10-times $LD_{100}$ of CFD2 were healthy after eleven days. The results indicated that fungal cells lacking FAS were unable to establish a systemic infection.

EXAMPLE 8—ISOLATION OF PATULODIN

A 12 liter fermentation of CK2108 was extracted as described in Example 1. The material that was insoluble in the CPC solvent of Example 1 was isolated by vacuum filtration and chromatographed by silica gel flash column chromatography eluted with increasing concentrations of ethyl acetate in hexane. One fraction isolated by this technique was determined by NMR to be patulodin.

EXAMPLE 9—SEPHADEX LH-20 PURIFICATION OF COMPOUND B

Extract material that was soluble in the CPC solvent was dried, redissolved in methanol and chromatographed on Sephadex LH-20 (Pharmacia, Uppsala, Sweden) using methanol as the eluent. The major peak from this fractionation was dried, redissolved in the two-phase mixture of CPC solvents, and subjected to the CPC chromatography described in Example 1.

EXAMPLE 10—FAS INHIBITION BY COMPOUND B

*C. Albicans* strain 4918 (available from Dr. Ronald Cihlar, Georgetown University Medical Center, Washington, D.C.) was grown in minimal medium (M63 media available from Difco, Detroit, Mich.) at 37° C. to mid-log phase. 10 μg/ml cerulenin and 25 μg/ml of compound B were added to separate cultures. At 15 minute intervals, 20 ml samples were removed and extracts prepared by mechanical extraction as in Example 1C, except that the ammonium sulfate precipitation step was not applied. The extract was diluted to 1 ml to form a solution containing 0.4M potassium phosphate, pH 7.3, 0.125 μM dithiothreitol, 50 μM acetyl-CoA, 100 μM NADPH. After incubation at 37° C. for 5 minutes, 100 μM malonyl-CoA containing 0.5 μCi [2-$^{14}$C]-malonyl-CoA (Amersham, Arlington Heights, Ill.). After 10 minutes at 37° C., the fatty acid synthesis reaction was terminated by adding 30 μl of 60% perchloric acid (v/v) and 1 ml ethanol. Four volumes of pet. ether were added to each reaction incubation to extract the fatty acids. The relative incorporation of malonyl-CoA into fatty acids was determined by liquid scintillation counting. The results were as follows:

| Time of Treatment | Percent Remaining FAS Activity | |
| --- | --- | --- |
| (minutes) | Cerulenin | Compound B |
| 15 | 20 | 53 |
| 30 | 12 | 40 |
| 45 | N.D. | 35 |
| 60 | N.D. | 22 |

We claim:

1. A method of treating a fungal infection comprising administering to an animal having a fungal infection a composition comprising an infection treating effective amount of a compound of formula I:

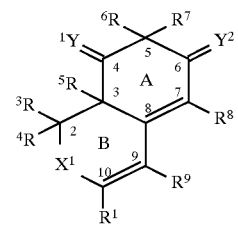

or a pharmaceutically acceptable salt thereof, wherein (1) $Y^1$ and $Y^2$ are independently O or S;

(2) $R^1$
  (i) is a straight-chained aliphatic group having about 2 to about 12 carbon atoms,
  (ii) the aliphatic group which additionally comprises an about 3 to about 8-membered carbocyclic ring consisting of three or more additional carbon atoms, or
  (iii) the aliphatic group which additionally comprises an about 3 to about 8-membered heterocyclic ring, wherein the heterocyclic ring contains up to 4 nitrogen atoms, up to 2 sulfur atoms, up to 2 oxygen atoms or additional carbon atoms, (2a) wherein the carbocyclic or heterocyclic ring atoms can have 1 to 4 substituents chosen from one or more of the following groups fluoro, chloro, bromo, iodo, hydroxy, (C1–C6) alkoxy, (C1–C6) alkyl, amino which c an be substituted with one or two (C1–C3) alkyl groups, nitro, aminocarbonyl which can be N-substituted with one or two (C1–C6) alkyl groups, alkylcarbonyloxy wherein alkyl can be C1–C6, alkoxycarbonyl wherein alkoxy can be C1–C6, hydroxycarbonyl, cyano, (C1–C3) alkylsulfonamido, (C1–C3) haloalkylsulfonamido which can be fully or partially halogenated wherein halo is fluoro, chloro, bromo or iodo, (C1–C8) alkanoylamino, (C1–C3) haloalkyl, which can be fully or partially halogenated wherein halo is fluoro, chloro, bromo or iodo, and alkanoylalkyl wherein alkanoyl is C2–C6 and alkyl is C1–C6;

(2b) wherein the non-ring portions of the straight-chained aliphatic group can be substituted with up to 4 of a (C1–C6) aliphatic group, fluoro, chloro, bromo, iodo, hydroxy, (C1–C6) alkoxy, amino which can be substituted with one or two (C1–C3) alkyl groups, nitro, aminocarbonyl which can be N-substituted with one or two (C1–C6) alkyl groups, alkylcarbonyloxy wherein alkyl can be C1–C6, alkoxycarbonyl wherein alkoxy can be C1–C6, hydroxycarbonyl, cyano, (C1–C3) alkylsulfonamido, (C1–C3) haloalkylsulfonamido which can be fully or partially halogenated wherein halo is fluoro, chloro, bromo or iodo, (C1–C8) alkanoylamino, (C1–C6) alkyl, (C1–C3) haloalkyl, which can be fully or partially halogenated wherein halo is fluoro, chloro, bromo or iodo, or alkanoylalkyl wherein alkanoyl is C2–C6 and alkyl is C1–C6;

(3) X is oxygen or sulfur or $NR^2$;

(4) $R^2$ is hydroxy, amino which can be substituted with one or two (C1–C8) alkyl groups, (C1–C8) alkyl, (C7–C10) arylalkyl, (C1–C8) alkoxy, (C1–C8) alkanoylamino or aminocarbonyl which can be N-substituted with one or two (C1–C8) alkyl groups, wherein $R^2$ can be substituted with up to 4 of alkylcarbonyloxy wherein alkyl can be C1–C6, alkoxycarbonyl wherein alkoxy can be C1–C6, hydroxycarbonyl, fluoro, chloro, bromo, iodo, hydroxy, (C1–C3) alkoxy, amino which can be substituted with one or two (C1–C6) alkyl groups, nitro, aminocarbonyl which can be N-substituted with one or two (C1–C6) alkyl groups, cyano, (C1–C3) alkylsulfonamido, (C1–C8) alkanoylamino, (C1–C3) haloalkylsufonamido, (C1–C3) alkyl, (C1–C3) haloalkyl, or alkanoylalkyl wherein alkanoyl is C2–C3 and alkyl is C1–C3;

(5) $R^3$ and $R^5$ either (a) each represent a half bond that together forms a double bond, or (b) $R^3$ is hydrogen and $R^5$ is hydrogen, aliphatic group having 1 to 3 carbons, fluoro, chloro, bromo, iodo, nitro, cyano, hydrocarbonyl, alkylcarbonyloxy wherein alkyl can be C1–C6, alkoxycarbonyl wherein alkoxy can be C1–C6, hydroxycarbonyl, (C1–C8) alkoxy, (C1–C8) alkanoylamino, (C1–C5) alkylsulfonamido, hydroxy, amino which can be substituted with one or two (C1–C3) alkyl groups, aminocarbonyl that can be N-substituted with one or two (C1–C6) alkyl groups, (C1–C3) haloalkylsulfonamido, (C1–C3) haloalkyl, or alkanoylalkyl wherein alkanoyl is C2–C3 and alkyl is C1–C3;

(6) $R^4$ is an aliphatic group having 1 to 3 carbons, cyano, hydroxycarbonyl, alkylcarbonyloxy wherein alkyl can be C1–C6, or alkoxycarbonyl wherein alkoxy can be C1–C6;

(7) $R^8$ and $R^9$ are independently hydrogen, aliphatic group having 1 to 3 carbons, fluoro, chloro, bromo, iodo, nitro, cyano, carboxyaldhyde, hydroxycarbonyl, alkylcarbonyloxy wherein alkyl can be C1–C6, alkoxycarbonyl wherein alkoxy can be C1–C6, (C1–C8) alkoxy, (C1–C8) alkanoylamino or (C1–C5) alkylsulfonamido;

(8) $R^6$ is a (C1–C6) aliphatic group, (C6–C10) aryl, (C7–C10) aralkyl, or a (C1–C3) aliphatic group substituted with a 5 or 6-membered heteroaromatic ring having up to 4 heteroatoms comprising nitrogen, sulfur or oxygen atoms; and (9) $R^7$ is —O—$R^{10}$ or —O—(C=O)—$R^{11}$ where $R^{10}$ is a hydrogen or $R^{10}$ and $R^{11}$ are (9a) an aliphatic group with 1 to 6 carbons, which aliphatic group may be substituted with one to 3 of: hydroxy, fluoro, chloro, bromo, iodo, cyano, amino which can be substituted with one or two (C1–C3) alkyl groups, (C1–C6) alkanoylamino, hydroxycarbonyl, alkylcarbonyloxy wherein alkyl can be C1–C6, alkoxycarbonyl wherein alkoxy can be C1–C6, aminocarbonyl which can be N-substituted with one or two (C1–C6) alkyl groups, (C1–C5) alkylsulfonate which can be partially or fully halogenated wherein halo is fluoro, chloro, bromo or iodo, (C1–C3) alkoxy, nitro, (C1–C6) alkyl, (C1–C3) haloalkyl, alkanoylalkyl wherein alkanoyl is C2–C3 and alkyl is C1–C3, or hydrocarbonyl, and wherein the aliphatic group can be substituted with an aryl or heteroaryl group where the aryl or heteroaryl moiety comprises a 6 or 10-membered aromatic ring, of which up to 4 ring atoms can be nitrogen heteroatoms, (9a1) wherein the aryl or heteroaryl group can be substituted with up to 4 substituents selected from the group consisting of (C1–C3) aliphatic group, fluoro, chloro, nitro, cyano, carboxyaldhyde, carboxyl, alkylcarbonyloxy wherein alkyl can be C1–C6, alkoxycarbonyl wherein alkoxy can be C1–C6, aminocarbonyl which can be substituted with one or two (C1–C6) alkyl groups, amino, amino substituted with one or two (C1–C3) hydrocarbons, (C1–C6) alkanoylamino, hydroxy, (C1–C3) alkoxy, amino, (C1–C3) alkylsulfonate, (C1–C3) haloalkylsufonate, (C1–C3) haloalkyl, and alkanoylalkyl wherein alkanoyl is C2–C6 and alkyl is C1–C6 or (9b) an aryl or heteroaryl group where the aryl or heteroaryl group comprises a 6 or 10-membered aromatic ring, of which up to 4 ring atoms can be nitrogen, wherein the aryl or heteroaryl group can be substituted with up to 4 substituents selected from the group consisting of (C1–C3) alkyl, (C1–C3) alkenyl, fluoro, chloro, iodo, bromo, nitro, cyano, carboxyaldhyde, hydroxycarbonyl, alkylcarbonyloxy wherein alkyl can be C1–C6, alkoxycarbonyl wherein alkoxy can be C1–C6, aminocarbonyl which can be N-substituted with one or two (C1–C6) alkyl groups, amino, amino substituted with one or two (C1–C3) aliphatic groups, (C1–C6) alkanoylamino, carboxyl (C1–C6) ester, hydroxy, (C1–C3) alkoxy, (C1–C3) alkylsulfonamido, (C1–C3) haloalkylsulfonamido, (C1–C3) haloalkyl, or alkanoylalkyl wherein alkanoyl is C2–C3 and alkyl is C1–C3;

(p1) with the proviso that when $R^7$ is acetyl the compound differs from chrysodin by at least one of (a) the presence or absence of a methylene, (b) the presence of sulfur or nitrogen in the compound in place of an oxygen, (c) the presence of halo, hydroxy, alkoxy, amino, nitro, alkanoylamino, aminocarbonyl, substituted aminocarbonyl, alkoxycarbonyl, hydroxycarbonyl, cyano, alkylsulfonamido, haloalkylsulfonamido, mono or di-alkylamino, alkanoylalkyl or hydrocarbonyl or (d) the presence in $R^1$ or $R^7$ of a carbocyclic or heterocyclic ring.

2. The method of claim 1, wherein the heterocyclic ring of $R^1$ is a heteroaryl moiety.

3. The method of claim 2, wherein the heteroaryl moiety of $R^1$ or $R^7$ is a pyridyl, thienyl, furanyl, pyrazinyl, pyrrolyl, indolyl, pyrimidyl, thiazolyl, isothiazolyl, oxazolyl, isoxazolyl, triazolyl, tetrazolyl, quinolyl or isoquinolyl.

4. The method of claim 1, wherein the carbocyclic ring of $R^1$ is a aryl moiety.

5. The method of claim 4, wherein the aryl moiety of $R^1$ or $R^7$ is phenyl or naphthyl.

6. The method of treatment of claim 1, wherein $R^7$ includes at least one hydroxy.

7. The method of treatment of claim 1, wherein $R^{10}$ and $R^{11}$ are aliphatic groups having 1 to 3 carbons, which may be substituted as set forth above.

8. The method of treatment of claim 7, wherein $R^{10}$ and $R^{11}$ are substituted with at least one hydroxy.

9. The method of treatment of claim 1, wherein the aliphatic group of $R^1$ has from about 2 to about 6 carbons.

10. The method of treatment of claim 1, wherein the halo substituents are fluoro.

11. The method of treatment of claim 1, wherein the compound is according to formula II:

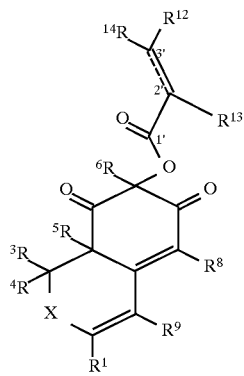

wherein the bond indicated by the parallel solid and broken lines can be a single or double bond where, if a double bond, it can be a cis or trans double bond, wherein $R^{12}$ is aminocarbonyl which can be substituted with one or two (C1–C6) alkyl groups, hydroxycarbonyl, alkoxycarbonyl wherein alkoxy can be C1–C6, alkylcarbonyloxy wherein alkyl can be C1–C6, or trifluoromethanesulfate, $R^{13}$ is hydrogen or C1 to C3 alkyl, and $R^{14}$ is hydrogen, C1 to C3 alkyl, or hydroxy.

12. A method of treating a fungal infection of claim 1, wherein $R^1$ conforms to one of the following formulas:

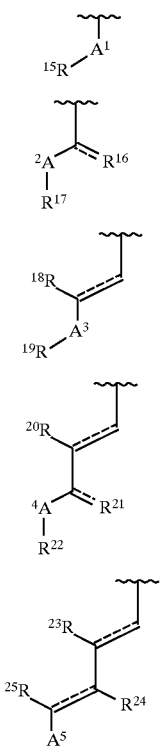

wherein the bonds represented with dashed lines are single or double bonds, $R^{15}$, $R^{17}$, $R^{19}$ and $R^{22}$ are (C1–C10) aliphatic groups, $R^{16}$, $R^{18}$, $R^{20}$, $R^{21}$, $R^{23}$, $R^{24}$ and $R^{25}$ are methyl, methylene or hydrogen, wherein $A^1$, $A^2$, $A^3$, $A^4$ and $A^5$ are six-membered aromatic or heterocyclic rings, having up to 4 nitrogen ring atoms and the rest carbon, $A^1$, $A^2$, $A^3$, $A^4$ and $A^5$ can be substituted with up to 4 substituents selected from the group consisting of fluoro, chloro, bromo, iodo, nitro, cyano, amino, (C1–C3) mono or di-alkylamino, (C1–C8) alkanoylamino, (C1–C3) alkylsulfonamido, (C1–C3) haloalkylsulfonamido which can be fully or partially halogenated wherein halo is fluoro, chloro, bromo or iodo, aminocarbonyl which can be substituted with one or two (C1–C6) alkyl groups, alkylcarbonyloxy wherein alkyl can be C1–C6, (C1–C6) alkoxycarbonyl, hydroxycarbonyl, (C1–C3) haloalkyl, which can be fully or partially halogenated wherein halo is fluoro, chloro, bromo or iodo, hydroxy, (C1–C8) alkoxy, and alkanoylalkyl wherein alkanoyl can be C2–C3 and alkyl can be C1–C3, and wherein the dashed lines indicate bonds that are either double or single bonds.

13. The method of treatment of claim 12, wherein $R^{15}$, $R^{17}$, $R^{19}$ and $R^{22}$ include an unsaturated bond conjugated to another unsaturated bond.

14. The method of treatment of claim 12, wherein the illustrated two bonds linking $A^1$, $A^2$, $A^3$, and $A^4$ are meta to each other.

15. The method of treatment of claim 12, wherein at least one of the dashed lines in each of formulas III–VII represents a double bond.

16. The method of treatment of claim 1, wherein $R^3$ and $R^5$ each represent a half bond that together forms a double bond, or $R^3$ is hydrogen and $R^5$ is hydrogen.

17. The method of treating of claim 1, wherein the microbial infection is a fungal infection.

18. The method of claim 17, wherein the fungal infection is caused by a fungus selected from the group consisting of fungi of the genus Candida, fungi of the genus Aspergillus, fungi of the genus Blastoschizomyces, fungi of the genus Cryptococcus, fungi of the genus Histoplasma, fungi of the genus Microsporum, fungi of the genus Sporothrix, fungi of the genus Torulopsis, fungi of the genus Trichophton, fungi of the genus Coccidioides such as *Coccidioides immitis*, fungi of the genus Epidermophyton such as *Epidermophyton floccosum* and fungi of the genus Mucor.

19. The method of claim 18, wherein the fungal infection is caused by a fungus selected from the group consisting *Candida tropicalis*, and *Mucor rouxii*.

20. The method of claim 17, wherein the fungal infection is caused by a fungus selected from the group consisting of fungi of the genus Aspergillus, fungi of the genus Cryptococcus, fungi of the genus Histoplasma, fungi of the genus Trichophton, and fungi of the genus Mucor.

21. A method of treating a microbial infection of claim 1 comprising administering to an animal infected with a microbe that expresses fatty acid synthetase a composition comprising an amount of a compound of formula I effective to inhibit said expressed fatty acid synthetase.

22. The method of claim 1, wherein the following proviso applies:

(p2) when $R^7$ is 2,4-dihydroxypentyl the compound of the invention differs from patulodin by at least one of (2a) the presence or absence of a methylene, (2b) the presence of sulfur or nitrogen in the compound in place of an oxygen, (2c) the presence of halo, hydroxyl, alkoxyl, amino, nitro, alkanoylamino, aminocarbonyl, substituted aminocarbonyl, alkoxycarbonyl, carboxylate, cyano, alkylsulfonamido, haloalkylsulfonamido, alkylamino, alkanoylalkyl or carboxyaldehyde or (2d) the presence in $R^1$ or $R^7$ of a carbocyclic or heterocyclic ring.

23. The method of claim 22, wherein the difference recited in (p1)(a) and (p2)(a) is at least two methylenes.

24. The method of claim 1, wherein the following proviso applies:

(p3) either the 7-position of the A ring is not substituted with chloro or the R1 position differs from a 3,5-dimethyl-hepta-1,3-dienyl group.

25. The method of claim 1, wherein the following proviso applies:
(p4) R7 is either (a) not one of 2-methyl-3,5-dihydroxyphenylcarbonyl or methyl or (b) R1 is not one of propyl-2-enyl, 1-hydroxypropyl-2-enyl or 1-carboxylethylenyl.

26. A composition comprising a compound according to:

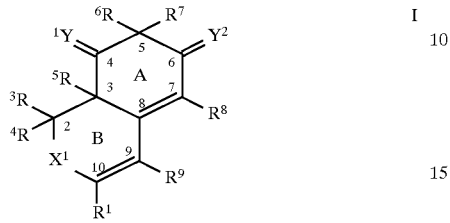

or a pharmaceutically acceptable salt thereof, wherein
(1) $Y^1$ and $Y^2$ are independently O or S;
(2) $R^1$
   (i) is a straight-chained aliphatic group having about 2 to about 12 carbon atoms,
   (ii) the aliphatic group which additionally comprises an about 3 to about 8-membered carbocyclic ring consisting of three or more additional carbon atoms, or
   (iii) the aliphatic group which additionally comprises an about 3 to about 8-membered heterocyclic ring, wherein the heterocyclic ring contains up to 4 nitrogen atoms, up to 2 sulfur atoms, up to 2 oxygen atoms or additional carbon atoms,
   (2a) wherein the carbocyclic or heterocyclic ring atoms can have 1 to 4 substituents chosen from one or more of the following groups fluoro, chloro, bromo, iodo, hydroxy, (C1–C6) alkoxy, (C1–C6) alkyl, amino which can be substituted with one or two (C1–C3) alkyl groups, nitro, aminocarbonyl which can be N-substituted with one or two (C1–C6) alkyl groups, alkylcarbonyloxy wherein alkyl can be C1–C6, alkoxycarbonyl wherein alkoxy can be C1–C6, hydroxycarbonyl, cyano, (C1–C3) alkylsulfonamido, (C1–C3) haloalkylsulfonamido which can be fully or partially halogenated wherein halo is fluoro, chloro, bromo or iodo, (C1–C8) alkanoylamino, (C1–C3) haloalkyl, which can be fully or partially halogenated wherein halo is fluoro, chloro, bromo or iodo, and alkanoylalkyl wherein alkanoyl is C2–C6 and alkyl is C1–C6;
   (2b) wherein the non-ring portions of the straight-chained aliphatic group can be substituted with up to 4 of a (C1–C6) aliphatic group, fluoro, chloro, bromo, iodo, hydroxy, (C1–C6) alkoxy, amino which can be substituted with one or two (C1–C3) alkyl groups, nitro, aminocarbonyl which can be N-substituted with one or two (C1–C6) alkyl groups, alkylcarbonyloxy wherein alkyl can be C1–C6, alkoxycarbonyl wherein alkoxy can be C1–C6, hydroxycarbonyl, cyano, (C1–C3) alkylsulfonamido, (C1–C3) haloalkylsulfonamido which can be fully or partially halogenated wherein halo is fluoro, chloro, bromo or iodo, (C1–C8) alkanoylamino, (C1–C6) alkyl, (C1–C3) haloalkyl, which can be fully or partially halogenated wherein halo is fluoro, chloro, bromo or iodo, or alkanoylalkyl wherein alkanoyl is C2–C6 and alkyl is C1–C6;
(3) X is oxygen or sulfur or $NR^2$;
(4) $R^2$ is hydroxy, amino which can be substituted with one or two (C1–C8) alkyl groups, (C1–C8) alkyl, (C7–C10) arylalkyl, (C1–C8) alkoxy, (C1–C8) alkanoylamino or aminocarbonyl which can be N-substituted with one or two (C1–C8) alkyl groups, wherein $R^2$ can be substituted with up to 4 of alkylcarbonyloxy wherein alkyl can be C1–C6, alkoxycarbonyl wherein alkoxy can be C1–C6, hydroxycarbonyl, fluoro, chloro, bromo, iodo, hydroxy, (C1–C3) alkoxy, amino which can be substituted with one or two (C1–C6) alkyl groups, nitro, aminocarbonyl which can be N-substituted with one or two (C1–C6) alkyl groups, cyano, (C1–C3) alkylsulfonamido, (C1–C8) alkanoylamino, (C1–C3) haloalkylsufonamido, (C1–C3) alkyl, (C1–C3) haloalkyl, or alkanoylalkyl wherein alkanoyl is C2–C3 and alkyl is C1–C3;
(5) $R^3$ and $R^5$ either (a) each represent a half bond that together forms a double bond, or (b) $R^3$ is hydrogen and $R^5$ is hydrogen, aliphatic group having 1 to 3 carbons, fluoro, chloro, bromo, iodo, nitro, cyano, hydrocarbonyl, alkylcarbonyloxy wherein alkyl can be C1–C6, alkoxycarbonyl wherein alkoxy can be C1–C6, hydroxycarbonyl, (C1–C8) alkoxy, (C1–C8) alkanoylamino, (C1–C5) alkylsulfonamido, hydroxy, amino which can be substituted with one or two (C1–C3) alkyl groups, aminocarbonyl that can be N-substituted with one or two (C1–C6) alkyl groups, (C1–C3) haloalkylsulfonamido, (C1–C3) haloalkyl, or alkanoylalkyl wherein alkanoyl is C2–C3 and alkyl is C1–C3;
(6) $R^4$ is an aliphatic group having 1 to 3 carbons, cyano, hydroxycarbonyl, alkylcarbonyloxy wherein alkyl can be C1–C6, or alkoxycarbonyl wherein alkoxy can be C1–C6;
(7) $R^8$ and $R^9$ are independently hydrogen, aliphatic group having 1 to 3 carbons, fluoro, chloro, bromo, iodo, nitro, cyano, carboxyaldhyde, hydroxycarbonyl, alkylcarbonyloxy wherein alkyl can be C1–C6, alkoxycarbonyl wherein alkoxy can be C1–C6, (C1–C8) alkoxy, (C1–C8) alkanoylamino or (C1–C5) alkylsulfonamido;
(8) $R^6$ is a (C1–C6) aliphatic group, (C6–C10) aryl, (C7–C10) aralkyl, or a (C1–C3) aliphatic group substituted with a 5 or 6-membered heteroaromatic ring having up to 4 heteroatoms comprising nitrogen, sulfur or oxygen atoms; and
(9) $R^7$ is —O—$R^{10}$ or —O—(C=O)—$R^{11}$ where $R^{10}$ is a hydrogen or $R^{10}$ and $R^{11}$ are
   (9a) an aliphatic group with 1 to 6 carbons, which aliphatic group may be substituted with one to 3 of: hydroxy, fluoro, chloro, bromo, iodo, cyano, amino which can be substituted with one or two (C1–C3) alkyl groups, (C1–C6) alkanoylamino, hydroxycarbonyl, alkylcarbonyloxy wherein alkyl can be C1–C6, alkoxycarbonyl wherein alkoxy can be C1–C6, (C1–C6) aminocarbonyl which can be N-substituted with one or two (C1–C6) alkyl groups, (C1–C5) alkylsulfonate which can be partially or fully halogenated wherein halo is fluoro, chloro, bromo or iodo, (C1–C3) alkoxy, nitro, (C1–C6) alkyl, (C1–C3) haloalkyl, alkanoylalkyl wherein alkanoyl is C2–C3 and alkyl is C1–C3, or hydrocarbonyl, and wherein the aliphatic group can be substituted with an aryl or heteroaryl where the aryl or heteroaryl moiety comprises a 6 or 10-membered aromatic ring, of which up to 4 ring atoms can be nitrogen heteroatoms,
   (9a1) wherein the aryl or heteroaryl group can be substituted with up to 4 substituents selected from the group consisting of (C1–C3) aliphatic group, fluoro, chloro, nitro, cyano, carboxyaldhyde, carboxyl, alkylcarbonyloxy wherein alkyl can be C1–C6, alkoxycarbonyl wherein alkoxy can be C1–C6, aminocarbonyl which can be substituted with one or two (C1–C6) alkyl groups, amino, amino substituted with one or two (C1–C3) hydrocarbons, (C1–C6) alkanoylamino, hydroxy, (C1–C3) alkoxy, amino, (C1–C3) alkylsulfonate, (C1–C3) haloalkylsufonate, (C1–C3) haloalkyl, and alkanoylalkyl wherein alkanoyl is C2–C6 and alkyl is C1–C6 or (9b) an aryl or heteroaryl group where the aryl or heteroaryl group comprises a 6 or 10-membered aromatic ring, of which up to 4 ring atoms can be nitrogen, wherein the aryl or heteroaryl group can be substituted with up to 4 substituents selected from the group consisting of (C1–C3) alkyl, (C1–C3) alkenyl, fluoro, chloro, iodo, bromo, nitro, cyano, carboxyaldhyde, hydroxycarbonyl, alkylcarbonyloxy wherein alkyl can be C1–C6, alkoxycarbonyl wherein alkoxy can be C1–C6, aminocarbonyl which can be N-substituted with one or two (C1–C6) alkyl groups, amino, amino substituted with one or two (C1–C3) aliphatic groups, (C1–C6) alkanoylamino, carboxyl (C1–C6) ester, hydroxy, (C1–C3) alkoxy, (C1–C3) alkylsulfonamido, (C1–C3) haloalkylsulfonamido, (C1–C3) haloalkyl, or alkanoylalkyl wherein alkanoyl is C2–C3 and alkyl is C1–C3;

(p1) with the proviso that when $R^7$ is acetyl the compound differs from chrysodin by at least one of (a) the presence or absence of a methylene, (b) the presence of sulfur or nitrogen in the compound in place of an oxygen, (c) the presence of halo, hydroxy, alkoxy, amino, nitro, alkanoylamino, aminocarbonyl, substituted aminocarbonyl, alkoxycarbonyl, hydroxycarbonyl, cyano, alkylsulfonamido, haloalkylsulfonamido, mono or di-alkylamino, alkanoylalkyl or hydrocarbonyl or (d) the presence in $R^1$ or $R^7$ of a carbocyclic or heterocyclic ring (p2) with the further proviso that when $R^7$ is 2,4-dihydroxypentyl the compound of the invention differs from patulodin by at least one of (a) the presence or absence of a methylene, (b) the presence of sulfur or nitrogen in the compound in place of an oxygen, (c) the presence of halo, hydroxyl, alkoxyl, amino, nitro, alkanoylamino, aminocarbonyl, substituted aminocarbonyl, alkoxycarbonyl, carboxylate, cyano, alkylsulfonamido, haloalkylsulfonamido, alkylamino, alkanoylalkyl or carboxyaldehyde, (d) the presence in $R^1$ or $R^7$ of a carbocyclic or heterocyclic ring or (e) the absence of an epoxide moiety;

(p3) with the further proviso that either the 7-position of the A ring is not substituted with chloro or the $R^1$ position differs from a 3,5-dimethyl-hepta-1,3-dienyl group; and (p4) with the further proviso that $R^7$ is either (a) not one of 2-methyl-3,5-dihydroxy-phenylcarbonyl or methyl or (b) $R^1$ is not one of propyl-2-enyl, 1-hydroxypropyl-2-enyl or 1-carboxyl-ethylenyl.

27. A pharmaceutical composition according to claim 26 comprising a pharmaceutically acceptable diluent or excipient.

28. The pharmaceutical composition according to claim 27 comprising liposomes containing said compound.

* * * * *